United States Patent [19]
Hudson et al.

[11] Patent Number: 5,264,644
[45] Date of Patent: Nov. 23, 1993

[54] PREPARATION OF CONJUGATED DIENES

[75] Inventors: Ian D. Hudson, Freckleton; Graham J. Hutchings, Osmotherley, both of United Kingdom

[73] Assignee: Enichem Elastomers Limited, United Kingdom

[21] Appl. No.: 14,058

[22] Filed: Feb. 5, 1993

Related U.S. Application Data

[63] Continuation of Ser. No. 708,897, May 31, 1991, abandoned.

[30] Foreign Application Priority Data

Jun. 4, 1990 [GB] United Kingdom ............... 9012429

[51] Int. Cl.$^5$ .............................................. C07C 1/207
[52] U.S. Cl. ............................................................ 585/606
[58] Field of Search .......................................... 585/606

[56] References Cited

U.S. PATENT DOCUMENTS

| | | | |
|---|---|---|---|
| 1,033,180 | 7/1912 | Kyriakides et al. | 585/606 |
| 4,310,440 | 1/1982 | Wilson et al. | 585/481 |
| 4,524,233 | 6/1985 | Hsu et al. | 585/606 |
| 4,547,614 | 10/1985 | Vavere | 585/606 |
| 4,587,372 | 5/1986 | Hsu | 585/606 |
| 4,628,140 | 12/1986 | Wideman | 585/606 |
| 4,632,913 | 12/1986 | Hsu | 502/202 |
| 4,734,538 | 3/1988 | O'Conner et al. | 585/606 |

FOREIGN PATENT DOCUMENTS

| | | |
|---|---|---|
| 80449 | 8/1983 | European Pat. Off. . |
| 721116 | 3/1980 | U.S.S.R. . |
| 1385348 | 2/1973 | United Kingdom . |
| 2063297 | 6/1981 | United Kingdom . |
| 2063060 | 8/1982 | United Kingdom . |

OTHER PUBLICATIONS

J. B. Moffat, Rev. Chem. Intermediates (1987) vol. 8, pp. 1-20.
Irodov et al, Zh. Org Khim (1982), vol. 18, pp. 1218-1220.
V. A. Mazaeva et al. Neftekhimiya (1990) vol. 30(2), pp. 211-214.
D. A. Bol'shakov et al. Prom Sint Kauchuka 8, 2, 1980.
Forster et al. Chem. Tech. 16 No. 12 746, 1986.

*Primary Examiner*—Asok Pal
*Attorney, Agent, or Firm*—Wood, Herron & Evans

[57] ABSTRACT

The invention relates to a process for the preparation of a conjugated diene from the corresponding carbonyl compound having the same number of carbon atoms by dehydration at a temperature of 300° to 450° C. using a catalyst comprising aluminium phosphate having the cristobalite structure. This catalyst is superior to aluminium phosphate having the tridymite structure in the dehydration of carbonyl compounds and has advantages over boron phosphate catalysts. Using the process, isoprene may be prepared from 2-methyl butanal and/or methyl isopropyl ketone in high yields. Unexpectedly aluminium phosphate having the cristobalite structure is markedly superior to boron phosphate in converting methyl isopropyl ketone, which is an intermediate product formed in appreciable amounts in the dehydration of 2-methyl butanal to isoprene. This superiority significantly improves the process economics of the conversion reaction of 2-methyl butanal to isoprene.

10 Claims, 4 Drawing Sheets

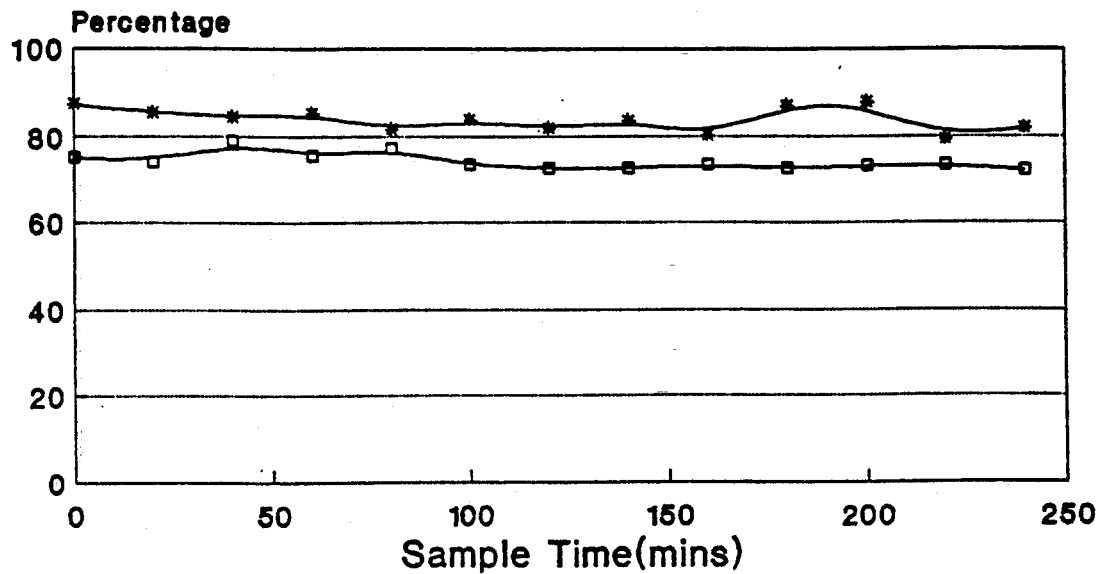
FIG.1  Reaction Over Catalyst  AP1A
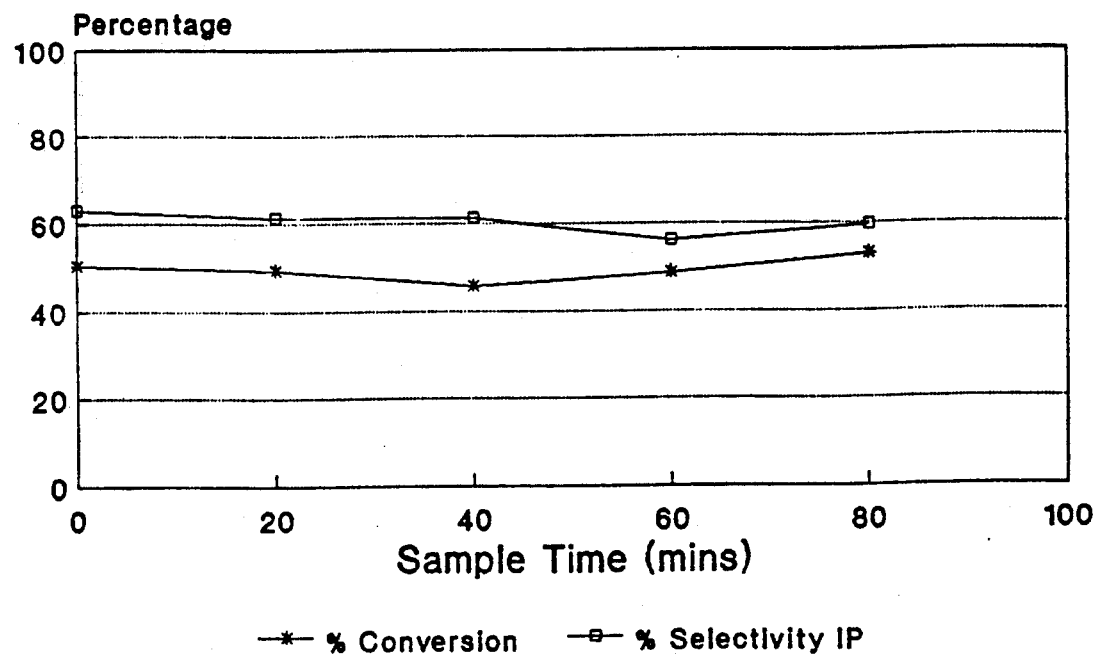
FIG.2  Reaction Over Catalyst  AP1B
—*— % Conversion    —□— % Selectivity IP

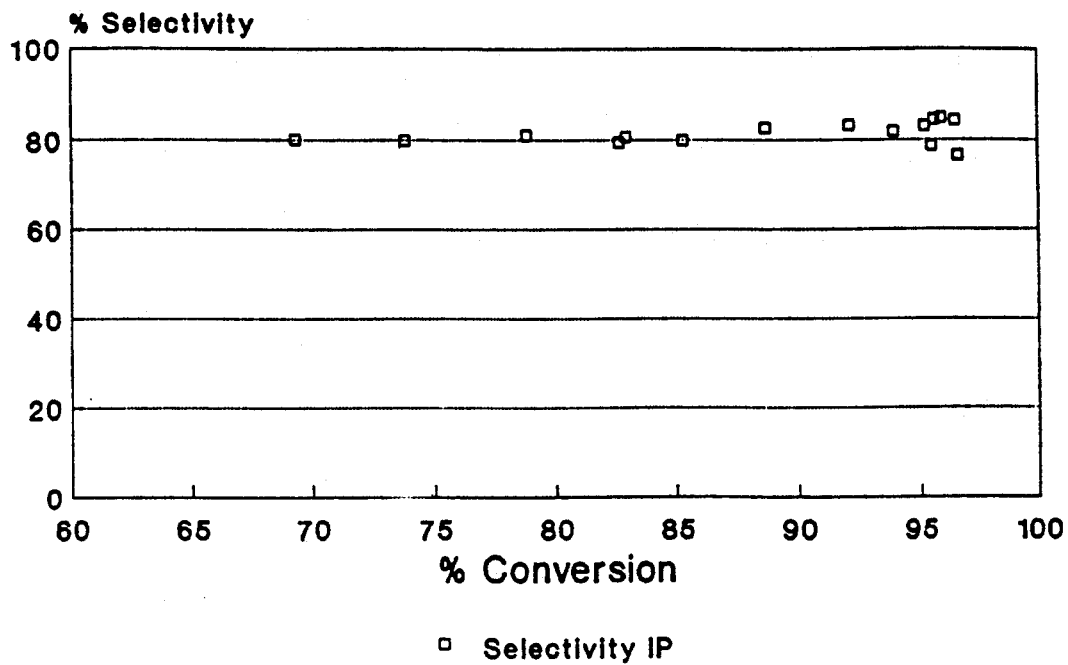
FIG.3 Conversion Versus Selectivity Reaction of 2MB with AP1A at 400°C
□ Selectivity IP
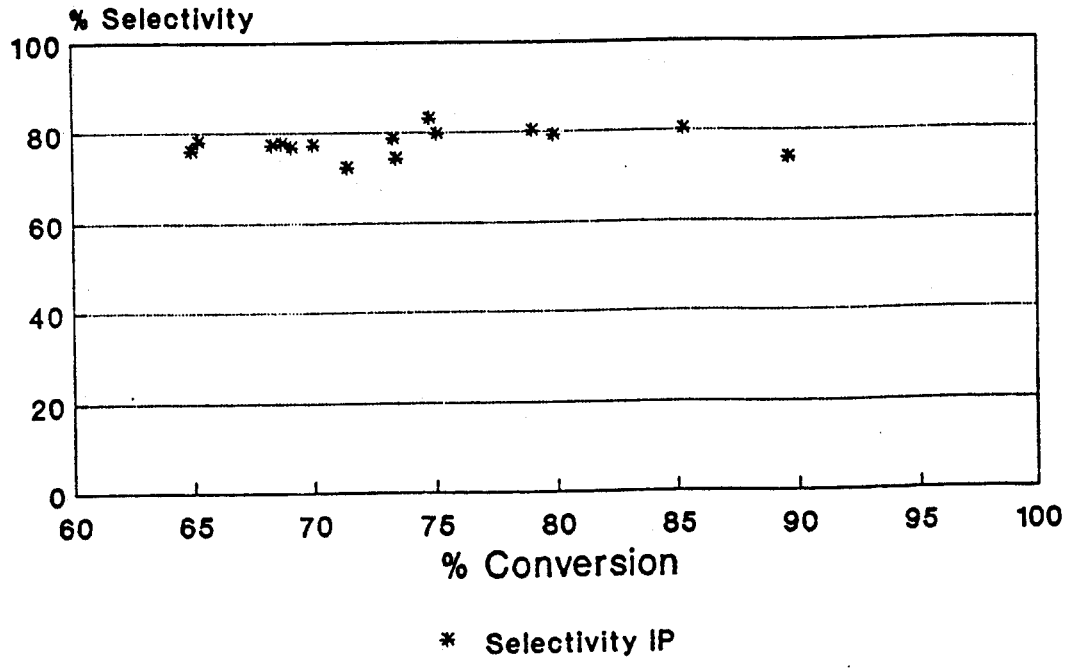
FIG.4 Conversion Versus Selectivity Reaction of 2MB with DBP11 at 325°C
∗ Selectivity IP FIG. 5   Reaction of 2MIPK with AP1A at 400° C and 0.1ml/hr
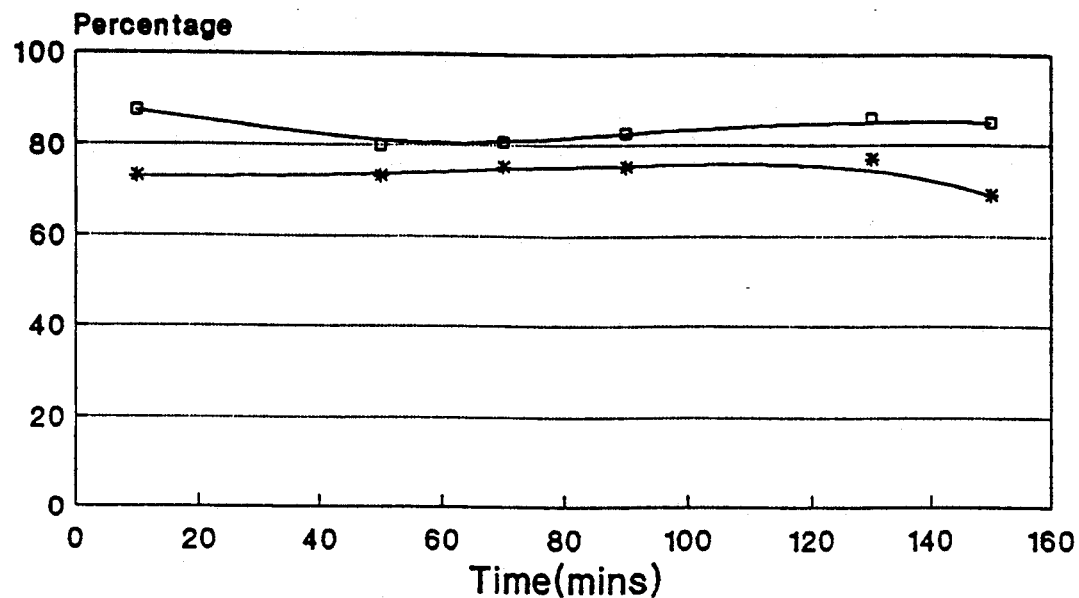
FIG. 6   Reaction of 2MIPK with DBP11 at 325° C and 0.1ml/hr
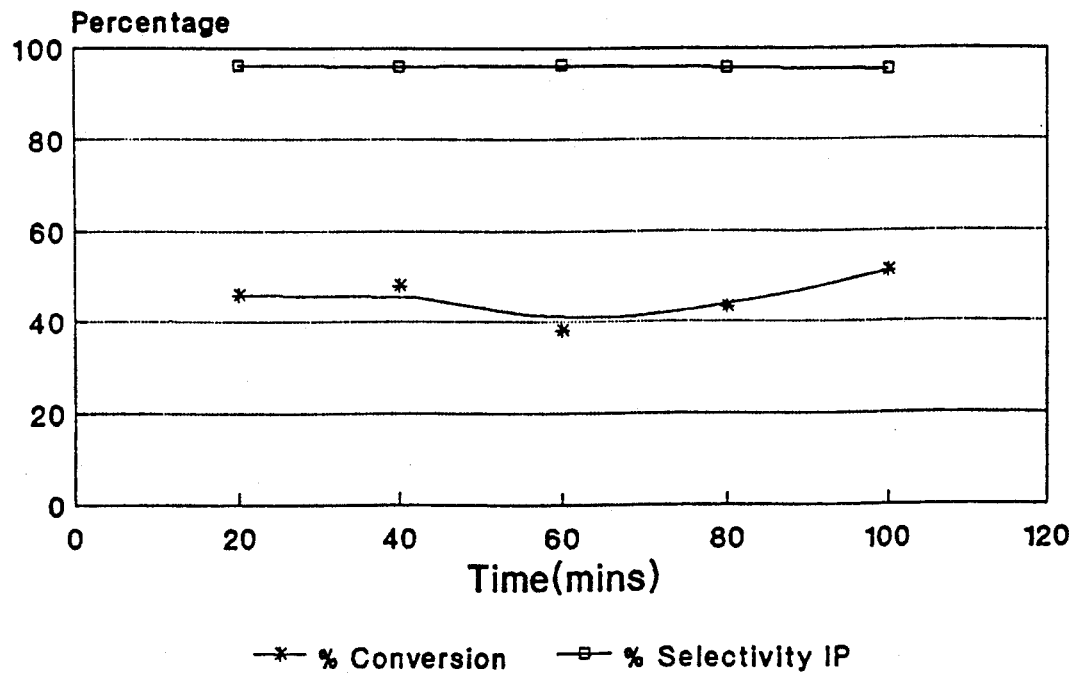
—*— % Conversion   —□— % Selectivity IP

FIG. 7 *Reaction of 2MIPK with AP1A at 400°C and 0.2ml/hr*
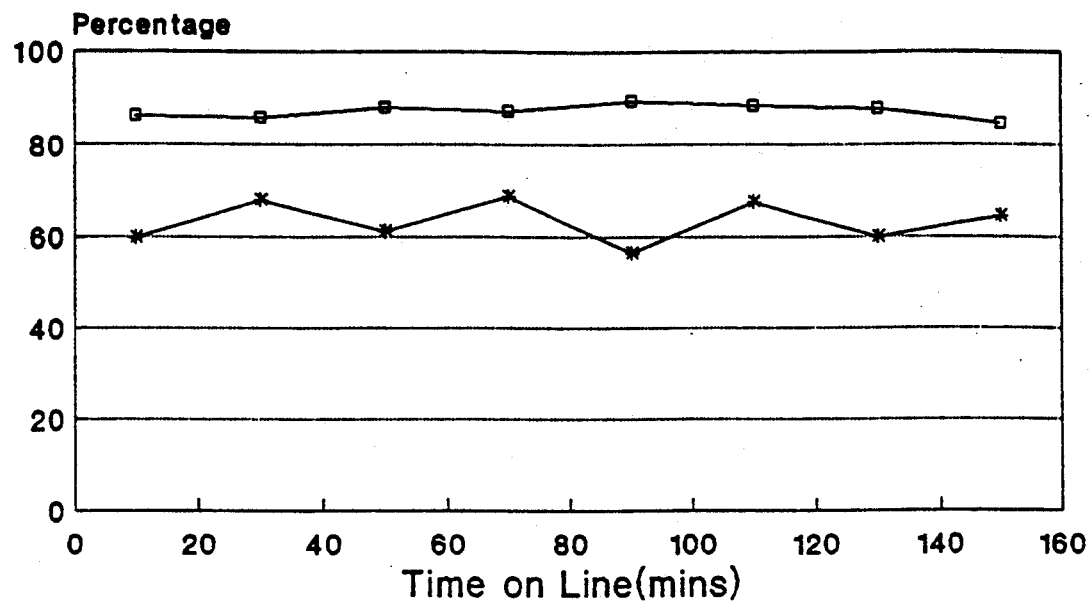
FIG. 8 *Reaction of 2MIPK with DBP11 at 325°C and 0.2ml/hr*
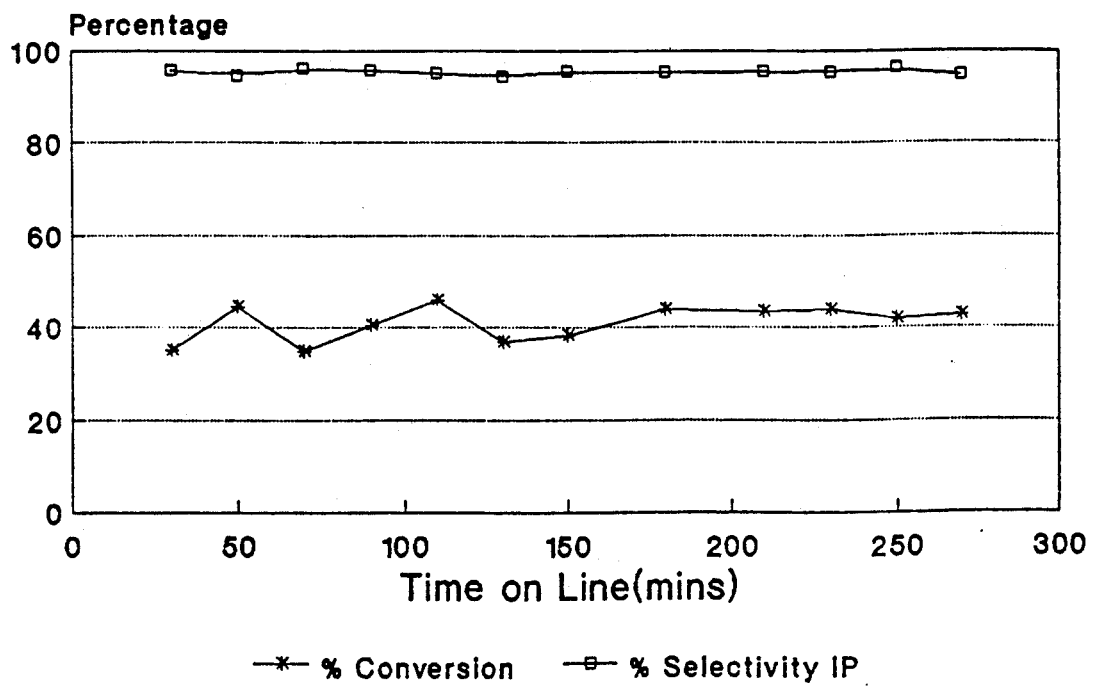
—✱— % Conversion   —▫— % Selectivity IP

PREPARATION OF CONJUGATED DIENES

This application is a continuation of application Ser. No. 07/708,897, filed May 31, 1991, now abandoned.

FIELD OF THE INVENTION

This invention relates to the preparation of a conjugated diene by dehydration of the corresponding carbonyl compound having the same number of carbon atoms and to a catalyst for the dehydration reaction. Conjugated dienes, especially butadiene and isoprene, are important monomers for the synthetic rubber industry. In a preferred embodiment, this invention relates to the preparation of isoprene by the dehydration of 2-methyl butyraldehyde (2-methylbutanal).

BACKGROUND OF THE INVENTION

Isoprene may be obtained as a by-product from naphtha cracking by extraction from pyrolysis fractions or it may be synthesised by a number of routes. Synthetic routes to isoprene have been comprehensively reviewed in the literature (see, for example, M J Rhoad, Rubber Ind (London) 9 (12), 68 (1975); E Schoenberg, H A Marsh, S J Walters and W M Saltman, Rubber Chem Tech 52, 526 (1979) and D L Schultz, Ed, Rubber World 179 (7), 87 (1980)). Extraction, dehydrogenation of isoamylene or isopentane and synthesis from acetylene/acetone or isobutene and formaldehyde are the usual processes to obtain isoprene, commercially. A high proportion of commercial production is obtained by extraction.

Recently, interest has turned to a process for the synthesis of isoprene form linear butenes by isomerisation of mixed linear butenes, hydroformylation of the butene-2-mixture to 2-methylbutanal and dehydration of the 2-methylbutanal (see, for example, Proceedings 26th Assembly of International Rubber Study Group, Kuala Lumpur 29th Sep.–4 Oct. 1980, 218; D A Bol'shakov et al, Prom Sint Kauchuka 8, 2 (1980), European Patent No. 80449 and Forster, D; Sluka, J P and Vavere A Chemtech 16 No. 12 746, 1986). The commercial attraction of this process is the availability of large quantities of linear butenes as a raffinate int he production of methyl tertiary butyl ether (MTBE) as an octane booster for petrol. A process for producing isoprene by dehydration of valeraldehyde (2-methyl butanal) using aluminium silicate at 400° to 600° C. was first disclosed in U.S. Pat. No. 1,033,180 (1911). Much more recently, British Patent No. 1,385,348 (Erdolchemie) discloses a process for the catalytic production of dienes from aldehydes by dehydration using an acidic dehydration catalyst. Boron phosphate is a particularly preferred dehydration catalyst for the process. USSR Inventors Certificate No. 721116 (Bolshakov et al) discloses a method for the preparation of boron phosphate for the production of isoprene, the invention relating to a method of obtaining a boron phosphate catalyst with enhanced activity and selectivity. Other improved boron phosphate catalysts and/or improved processes for their use in the dehydration reaction have been described in U.S. Pat. Nos. 4,524,233, 4,587,372, 4,632,913 and 4,628,140 (all Goodyear Tire & Rubber) and U.S. Pat. No. 4,547,614 (Monsanto). The conversion of 2-methylbutanal to isoprene using boron phosphate catalysts has been extensively studied by Moffat and co-workers (see, for example, J B Moffat Rev. Chemical Intermediates 8 1 (1987)). Although boron phosphate catalysts exhibit high conversions and selectivities, they deactivate very rapidly and long term effective reactivation techniques have not been disclosed in the literature. Catalysts, other than boron phosphate, which have been investigated for this dehydration reaction include an alum or a mixed sulphate derived therefrom (British Patent No. 2,063,297) and magnesium ammonium phosphate (British Patent No. 2,093,060). Irodov, A V, Smirnov, V A and Kryrukov S I Zh Org Khim, 18 1401 (1982) describe the study of a number of catalysts based on the phosphates of aluminium, boron and calcium although the results reported relate only to calcium phosphate catalyst. A wide variety of catalysts including $Be_3(PO_4)_2$, $Mg_3(PO_4)_2$, $Si_3(PO_4)$, $Ba_3(PO_4)_2$ and $AlPO_4$ et al, was studied by Maraeva V A et al, Neftekhim 30 (2) 211 (1990). The use of zerolites as dehydration catalyst has been disclosed in U.S. Pat. No. 4,560,822 and European Patent No. 219, 042 (BASF) as well as U.S. Pat. No. 4,734,538 and European Pat. No. 272,662 (Union Carbide).

SUMMARY OF THE INVENTION

According to the present invention a process for the preparation of a conjugated diene from the corresponding carbonyl compound having the same number of carbon atoms comprises contacting the carbonyl compound at a temperature of 300° C. to 450° C. with a catalyst comprising aluminium phosphate having the cristobalite structure. The invention also includes a process for the preparation of a conjugated diene from the corresponding carbonyl compound having the same number of carbon atoms which comprises contacting the carbonyl compound at a temperature of 300° C. to 450° C. with a catalyst comprising aluminium phosphate obtained by reaction of an aluminium salt and a phosphorus compound followed by calcination at a temperature of at least 300° C. for 1 hour or more, the starting materials and reaction conditions being such that the aluminium phosphate product comprises at least some, preferably 25% or more, of crystobalite structure. Aluminium phosphate is capable of existing in six different structures analogous to the six forms of silica. The type of phase occurring is dependent on the method of preparation and treatment temperature.

Phase: Quartz→Tridymite→Cristobalite→Melt $\beta \to \alpha\beta \to \alpha\beta \to \beta$ We have found that the crystal structure of the aluminium phosphate has a critical effect upon catalyst activity and selectivity in the dehydration of the carbonyl compound (hereinafter referred to as 'the dehydration reaction'). Thus aluminium phosphate having the cristobalite structure exhibits similar activity in the dehydration reaction, to boron phosphate though at a higher temperature in contrast to aluminium phosphate, which is all tridymite structure or substantially (e.g. 85% or more on a molar basis) tridymite structure, which shows much reduced conversions and selectivity in the dehydration reaction.

The aluminium phosphate used in the diene preparation need not be all cristobalite. A material which is a mixture of cristobalite and triydmite phases (1:1 molar), of predominately (i.e. is a major proportion of) cristobalite structure or of all cristobalite structure is preferred. However mixtures containing as little as 20% cristobalite, on a molar basis, give improvements in the dehydration reaction. Thus 20% cristobalite represents a practical minimum figure. The aluminium to phosphorus atomic ratio is preferably 1:1 or is such that there is a stoichiometric excess of phosphorus. One method for preparing aluminium phosphate of suitable structure is that described by Campelo J M et al J Catalysis 111, 106 (1988) incorporated herein by reference, starting form aluminium chloride but the invention is not restricted to the use of aluminium phosphate prepared by this method.

It is also possible to prepare mixed phosphates, for example a mixed aluminium/boron phosphate in which the aluminium phosphate comprises at least some cristobalite structure by incorporation of e.g. 5% to 40%, preferably 10% to 30% molar, of boron phosphate during the aluminium phosphate preparation and the invention specifically includes the use of such mixed phosphates in the dehydration reaction.

DESCRIPTION OF THE DRAWINGS

FIGS. 1 and 2 shows the percent conversion and percent selectivity for isoprene plotted against time in minutes for the conversion reactions using cristobalite/-tridymite AlPO$_4$ (sample APIA) and the all tridymite sample (APIB) as described in Example 1.

FIGS. 3 and 4 are graphs of percent selectivity against % conversion using variable flow rates of 2-methyl butanol feed using: FIG. 3 AlPO$_4$ (sample APIA) at 400° C.: FIG. 4 BPO$_4$ sample at 320° C. as described in Example 2.

FIGS. 5 and 6 are graphs of percent conversion and percent selectivity measured at various intervals of time using 2-methyl isopropyl ketone feed at a fixed flow rate of 0.1 ml/hr using: FIG. 5 AlPO$_4$ (sample APIA) at 400° C.: FIG. 6 BPO$_4$ sample at 325°, as described in Example 2.

FIGS. 7 and 8 are similar graphs of percent conversion and percent selectivity measured at various intervals of time using 2-methyl isopropyl ketone feed at a fixed flow rate of 0.2 ml/hr.

DETAILED DESCRIPTION OF THE INVENTION

In general terms, aluminium phosphate of the required structure is obtained by reaction of an aluminium salt and a phosphorus compound followed by calcination at a temperature of at least 300° C. for 1 hour or more. Reaction may be by controlled precipitation with alkali, preferably dilute aqueous ammonia, added slowly to an aqueous solution of the aluminium salt and the phosphorus compound, e.g. a phosphorus acid. Co-grinding of suitable starting materials, dry or by the paste method, is another possible route. Calcination is an important step in the catalyst preparation and is generally carried out at a temperature of at least 300° C. for a period of one hour or more. Temperatures considerably in excess of 300° C. are preferred, for example, 500° C. or more, preferably 650° C. to 1100° C., more preferably 750° C. to 1000° C. Calcination time is at least one hour but prolonged calcination, e.g. up to 8 hours, is not deleterious.

Irrespective of the particular method used to prepare the catalyst, the desired product preferably comprises at least 20% cristobalite structure. This can be established using powder x-ray diffraction. The structure corresponding to the orthorhombic symmetry of alpha cristobalite gives a characteristic peak, particularly at $2\theta-21.79$.

The surface area of the cristobalite aluminium phosphate catalyst should be as high as possible, for example 50 to 200 m$^2$/g, determined using the BET nitrogen adsorption method. In the process of the invention a carbonyl compound, preferably an aldehyde corresponding to the desired conjugated diene, is contacted with the catalyst at a temperature of 300° C. to 450° C. In general, carbonisation and undesired side reactions occur at higher temperatures. These should therefore be avoided. At lower temperatures than 300° C. the reaction is not so efficient and yields of the diene product are therefore much lower.

Using the process of the invention, the carbonyl compound, preferably an aldehyde, has the same number of carbon atoms as the desired conjugated diene, but as is known in the art, some isomers are easier to dehydrate than others. In the preparation of isoprene, 2-methyl butanal is the preferred starting material compared with 3-methyl butanal or 2,2-dimethyl propanal. In the preparation of isoprene form 2-methyl butanal, some methyl isopropyl ketone is formed and this is readily dehydrated to isoprene using the alpha cristobalite catalyst described herein.

Other suitable aldehydes are n-butanal, 2,3-dimethyl butanal and 2- or 3-ethyl butanal.

If desired an inert carrier gas such as nitrogen or carbon dioxide can be included with the carbonyl compound feed. By the process of the invention conjugated dienes, especially 1,3 butadiene and isoprene may be prepared in good yield and high selectivity.

The following examples illustrate the invention:

EXAMPLE 1

A. Catalyst Preparation

An aluminium phosphate (Al/P molar ratio=1) sample (APIA) was prepared from aluminium chloride and orthophosphoric acid using the procedure described by Campelo et al, J Catalysis 111, 106 (1988) at page 107.

To a cold aqueous solution containing an equal amount of aluminium chloride and orthophosphoric acid solution (0.985M) is dropwise added, with continuous stirring, a cold dilute aqueous ammonia solution (40% volume) until a white gel was precipitated and the pH of the supernatant became 7.0. The precipitate was then allowed to stand at room temperature for eighteen hours. The mixture was then filtered and the precipitate washed several times with propan-2-ol and then dried at 120° C. for twenty four hours. The resultant dried gel was screened at 200–250 mesh then calcined at 800° C. for three hours.

This sample (APIA) was characterised as being a mixture of alpha cristobalite and tridymite structures of approximately 30% cristobalite structure using powder x-ray diffraction and was also studied using Diffuse Reflectance Fourier Transform Infra-Red, X-Ray Photoelectron Spectroscopy and X-Ray Fluorescence.

The powder x-ray diffraction analysis was performed using a Philips x-ray diffractometer with Cu K$\alpha$ radiation ($\lambda=1.54178$ Å) at a scanning speed of 1° min$^{-1}$ giving the pattern shown in Table 1 and characterized using the diffraction patterns shown in F. d'Yvoire [Bull. Soc. Chem. France, 1/62 (1961)] at page 1775 which gives the full d-spacing figures for AlPO$_4$ cristobalite. This shows a very, very strong peak corresponding to d-spacing of 4.07 Å, and medium strong peaks corresponding to d—3.16 Å and 2.868 Å.

TABLE 1

Powder XRD of Mixed Tridymite/Cristobalite Aluminium Phosphate (APIA)

| 2θ | d Å | I |
|---|---|---|
| 20.435 | 4.3459 | 2349 |
| 21.580 | 4.1178 | 2616 |
| 21.799C | 4.0770C | 1358 |
| 23.087 | 3.9522 | 1526 |
| 25.172 | 3.5877 | 193 |
| 27.255 | 3.2719 | 810 |
| 28.208C | 3.1685C | 250 |
| 29.817 | 2.9964 | 326 |
| 31.180C | 2.8684C | 260 |
| 35.676 | 2.5165 | 490 |
| 37.395 | 2.4047 | 200 |

C denotes peak attributable to cristobalite

For comparison, a second aluminium phosphate sample (APIB) was prepared as described above but starting with aluminium sulphate instead of aluminium chloride. The dried gel was calcined at 500° C. for three hours. This sample (APIB) was characterised as being all tridymite structure using the same method as for sample APIA giving the x-ray diffraction pattern shown in Table 2.

TABLE 2

Powder XRD of Single Tridymite Aluminium Phosphate (APIB)

| 2θ | d Å | I |
|---|---|---|
| 7.890 | 11.2053 | 178 |
| 20.435 | 4.3458 | 998 |
| 21.601 | 4.1137 | 1236 |
| 22.946 | 3.8756 | 626 |
| 25.233 | 3.5293 | 290 |
| 35.668 | 2.5474 | 260 |

In addition, the surface area of each sample was measured using the BET method and was 93 m$^2$/g for sample (APIA) and 50 m$^2$/g for sample (APIB).

B. Catalyst Testing

A portion of the cristobalite/tridymite AlPO4 sample APIA was tested (Example 1a) in a microreactor for activity in the conversion of 2-methyl butanol to isoprene at 400° C. For comparison, a similar run was carried out using a portion of the all tridymite AlPO4, sample APIB (Example 1b). The reactions were carried out using a nitrogen carrier gas flow rate of 24 ml/minute and a flow rate of 0.2 ml/hr of 2-methyl butanal feed. The conversion and selectivity for the dehydration reactions were determined at intervals using an on-line gas chromatograph and mass spectrometry. The results are shown in FIGS. 1 and 2 which show the percent conversion and percent selectivity for isoprene plotted against time in minutes after raising the temperature from 370° C. initially.

By comparing FIGS. 1 and 2 it can be seen very clearly that the ristobalite/tridymite AlPO4 sample, APIA (FIG. 1) is considerably superior to the all tridymite sample, APIB (FIG. 2). In particular the high activity (in excess of 80%) compares with only about 50% for the all tridymite sample and selectivity (in excess of 70%) is superior.

EXAMPLE 2

In this example, portions of the aluminium phosphate cristobalite/tridymite sample (APIA) were tested for activity in the conversion of 2-methyl butanal and methyl isopropyl ketone to isoprene using the procedure of Example 1.

For comparison, similar runs were carried out at 325° C. using a boron phosphate catalyst (DBP.11) prepared from phosphoric acid and boric acid then calcined at 350° C. 325° C. is known to be the preferred operating temperature for boron phosphate in the dehydration reaction.

Results (% conversion and % selectivity) are shown in FIGS. 3 to 8 in which:

FIGS. 3 and 4 are graphs of % selectivity against % conversion using variable flow rates of 2-methyl butanal feed (increasing from 0.1 ml/hr to 0.8 ml/hr in steps of 0.1 m every 30 minutes).

FIG. 3 AlPO4 (sample APIA) at 400° C.

FIG. 4 BPO4 sample at 320° C.

In each case the nitrogen flow was 24 ml/min.

FIGS. 5 and 6 are graphs of % conversion and % selectivity measured at various intervals of time using 2-methyl isopropyl ketone feed at a fixed flow rate of 0.1 ml/hr.

FIG. 5 AlPO4 (Sample APIA) at 400° C.

FIG. 6 BPO4 sample at 325° C.

FIGS. 7 and 8 are similar graphs of % conversion and % selectivity measured at various intervals of time using 2-methyl isopropyl ketone feed at a fixed flow rate of 0.2 ml/hr.

From FIGS. 3 and 4 it can be seen that the activity/selectivity observed for the cristobalite/tridymite AlPO4 catalyst at 400° C. (FIG. 3) is comparable to that observed for boron phosphate at 325° C. (FIG. 4) in the conversion of 2-methyl butanal to isoprene.

From FIGS. 5, 6, 7 and 8 it can be seen that the activity for the cristobalite/tridymite AlPO4 catalyst at 400° C. (FIGS. 5 and 7) is broadly similar to that observed for boron phosphate at 325° C. (FIGS. 6 and 8) in the conversion of 2-methyl isopropyl ketone to isoprene. However the selectivity for isoprene is much superior when using the AlPO4 catalyst.

Unexpectedly the aluminium phosphate having the cristobalite structure is markedly superior to boron phosphate in converting methyl isopropyl ketone, which is an intermediate product in the dehydration of 2-methyl butanal, to isoprene. This superiority is an important advantage since, in this dehydration reaction, an appreciable amount of the ketone is formed and conversion of this intermediate to isoprene significantly improves the process economics of the conversion reaction starting from 2-methyl butanal.

EXAMPLE 3

A mixed aluminium/boron phosphate catalyst was prepared using the following procedure:

Aluminium chloride (12.0 g) in water (50 ml) was mixed with orthophosphoric acid, H3PO4, (85% solution, 5.2 ml) at 20° C. then boron phosphate (0.5 g) was added. The boron phosphate had been prepared previously by reacting boric acid and phosphoric acid in 1:1 molar ratio then calcining at 350° C. for 3 hours and shown to have the cristobalite structure using x-ray diffraction. To the mixed aluminium/boron reagent system, ammonium hydroxide was added gradually to bring the pH to 7. The mixed aluminium/boron phosphate precipitated and was left, without further treatment, open to air to age for 15 hours. The precipitate was separated by filtration, washed three times with isopropyl alcohol and dried at 120° C. for 16 hours. The product was calcined for three hours at 800° C. in air. The boron:aluminium molar ratio was found to be 0.05 mole BPO4:0.95 mole aluminium phosphate (i.e. 5% BPO4) and x-ray diffraction showed that the aluminium phosphate was a mixture of cristobalite/tridymite structures.

For comparison, a second sample was prepared using the same procedure but omitting the boron phosphate.

The mixed aluminium/boron phosphate and the comparison material (both having the cristobalite structure) were tested in the dehydration reaction at 325° C. using a flow rate of 2-methyl butanal of 0.2 ml/hr and a nitrogen carrier gas flow rate of 24 ml/min. The results showed that the mixed catalyst gave an enhanced yield of isoprene compared with the all AlPO4 catalyst.

We claim:

1. A process for the preparation of a conjugated diene from the corresponding carbonyl compound having the same number of carbon atoms which comprises contacting the carbonyl compound at a temperature of 300° C. to 450° C. with a catalyst comprising aluminium phosphate having the cristobalite structure.

2. A process according to claim 1 in which the catalyst comprises aluminium phosphate having at least 20% cristobalite structure on a molar basis.

3. A process according to claim 2 in which the catalyst is a mixture of cristobalite structure and tridymite structure in which the cristobalite structure predominates.

4. A process according to claim 1 in which the catalyst comprises a mixed aluminium phosphate/boron phosphate in which the aluminium phosphate comprises at least some cristobalite structure, prepared by incorporation of 5% –40% molar of boron phosphate during the aluminium phosphate preparation.

5. A process according to claim 1 in which the aluminium phosphate used as catalyst is obtained by reaction of an aluminium salt and a phosphorus compound followed by calcination at a temperature of at least 300° C. for one hour or more, the salt and compound and the reaction conditions being such that the aluminium phosphate product comprises at least some cristobalite structure.

6. A process according to claim 5 in which the calcination temperature is 500° C. or more.

7. A process according to claim 6 in which the calcination temperature is 650° C. to 1100° C.

8. A process according to claim 1 in which 2-methyl butanal is converted to isoprene.

9. A process according to claim 1 in which the catalyst has a powder x-ray diffraction pattern showing intense peaks corresponding to D-spacings around 4.7Å, 3.16 Å and 2.868 Å using a copper K$\alpha$ radiation source.

10. The process according to claim 1 wherein said aluminium phosphate has a surface area in the range of about 50 to about 200 m$^2$/g using the BET nitrogen adsorption method.

* * * * *

UNITED STATES PATENT AND TRADEMARK OFFICE
CERTIFICATE OF CORRECTION

PATENT NO. : 5,264,644
DATED : November 23, 1993
INVENTOR(S) : Ian D. Hudson & Graham J. Hutchings It is certified that error appears in the above-indentified patent and that said Letters Patent is hereby corrected as shown below:

Column 1, line 34, "form" should read -- from --.

Column 2, line 49, "$\beta \to \alpha\beta \to \alpha\beta \to \beta$" should read -- $\beta \to \alpha$ $\beta \to \alpha$ $\beta \to \alpha$ --.

Column 3, line 8, "form" should read -- from --.

Column 4, line 23, "form" should read -- from --.

Column 5, line 58, "ristobalite" should read -- cristobalite --.

Signed and Sealed this

Sixteenth Day of August, 1994

Attest:

BRUCE LEHMAN

Attesting Officer     Commissioner of Patents and Trademarks